United States Patent [19]

Bhatta

[11] Patent Number: 5,147,356
[45] Date of Patent: Sep. 15, 1992

[54] SURGICAL INSTRUMENT

[75] Inventor: Nayantara Bhatta, Brookline, Mass.

[73] Assignee: Microsurge, Inc., Needham, Mass.

[21] Appl. No.: 686,248

[22] Filed: Apr. 16, 1991

[51] Int. Cl.$^5$ .............................................. A61B 17/36
[52] U.S. Cl. ..................................... 606/37; 606/142; 606/167; 606/174
[58] Field of Search ........................ 606/1, 2, 8, 13-16, 606/36, 37, 39-52, 142-144, 167, 170-174, 205-211

[56] References Cited

U.S. PATENT DOCUMENTS

| 3,391,690 | 7/1968 | Armao | 606/184 |
| 3,439,523 | 4/1969 | Wood | 72/410 |
| 4,126,136 | 11/1978 | Auth et al. | 606/3 |
| 4,266,547 | 5/1981 | Komiya | 606/15 |
| 4,370,980 | 2/1983 | Lottick | 606/42 |

FOREIGN PATENT DOCUMENTS

| 0070459 | 1/1983 | European Pat. Off. |
| 2550693 | 5/1977 | Fed. Rep. of Germany |
| 3413520 | 10/1985 | Fed. Rep. of Germany |
| 1498474 | 8/1989 | U.S.S.R. |

OTHER PUBLICATIONS

"Combined Diathermy Forceps and Scissors" Stevenson, Oct. 1959.

Primary Examiner—Peter A. Aschenbrenner
Attorney, Agent, or Firm—Hayes, Soloway, Hennessey & Hage

[57] ABSTRACT

The invention provides a surgical instrument having a pair of opposed jaw members, at least one of which jaw members is moveable with respect to the other jaw member. A cutting and/or cauterizing heat source such as a hot wire element and/or laser transmission fiber is carried on at least one of the jaw members.

8 Claims, 2 Drawing Sheets

SURGICAL INSTRUMENT

BACKGROUND OF THE INVENTION

The present invention relates to improvements in surgical instruments. The invention has particular utility in connection with surgical instruments for use in cutting, clipping and/or coagulating and will be described in connection with such utility, although other utility is contemplated.

In the course of a surgical operation, a surgeon often must sever one or more blood vessels. It is desirable to provide means for closing the ends of severed vessels before the vessel is severed in order to stop bleeding which may interfere with the performance of the operation as well as present unnecessary risks of blood loss to the patient. As a result various surgical instruments have been developed and are available commercially for closing the ends of severed vessels to prevent bleeding by ligating or clamping off major blood vessels and cauterizing smaller blood vessels. For severing larger blood vessels, one preferred technique is the application of a pair of spaced hemostatic or ligating clips to the blood vessel and then severing the blood vessel between the spaced ligating clips. An example of an instrument used for such ligating clip application is described in U.S. Pat. No. 3,439,523 issued Apr. 22, 1969 to Ernest C. Wood. As taught by Wood, a magazine may be provided for mounting a plurality of ligating clips in position to be loaded between the jaws of the instrument whereby to permit application of a large number of ligating clips to various blood vessels to be clamped off. Actual cutting of the tissue and severing of the blood vessels may be accomplished using a conventional scalpel or a laser scalpel such as shown in U.S. Pat. No. 4,266,547 to Komiya. Alternatively, surgical scissors may be employed to cut the tissue and to sever the blood vessels. Using a laser scalpel has an advantage in that small blood vessels may be severed and cauterized in a single step.

BRIEF SUMMARY OF THE INVENTION

In broad aspect, the present invention provides a surgical instrument which comprises a pair of opposed jaw members, at least one of which jaw members is moveable with respect to the other jaw member, and including a cutting and cauterizing heat source such as a hot wire and/or laser transmission means operatively disposed on or adjacent at least one of the jaw members.

In one embodiment of the present invention, the jaw members are adapted to apply hemostatic clips, and comprise a cutting and/or cauterizing heat source such as a hot wire and/or laser transmission means operatively disposed on or adjacent at least one of the jaw members. Combining hemostatic clip application and cutting and/or cauterizing functions in a single instrument facilitates surgical procedures in that a single instrument may be used to perform both ligating and cutting operations. In another embodiment of the present invention, one of the jaw members comprises a sharpened blade and the other an anvil, or the jaw members comprise a pair of sharpened blades at least one of which is moveable with respect to the other, and a cutting and/or cauterizing heat source such as a hot wire or laser transmission means is operatively disposed on or adjacent one or both blades. In yet another embodiment of the present invention, the jaw members comprise a pair of forceps tongs at least one of which is moveable with respect to the other, and including a cutting and/or cauterizing heat source such as hot wire or laser transmission means operatively disposed on or adjacent one or both jaw members.

In a preferred form of the invention in which the surgical instrument comprises a ligating clip applicator and the cutting and/or cauterizing heat source is carried operatively disposed on or adjacent one or both clip applicator jaw members so that the cutting and cauterizing heat source can be manipulated along with the ligating clip applicator itself. Thus, after a vessel is clamped off by application of a pair of ligating clips, the heat source may be activated to sever the vessel in between the clips. Thus, it is possible to clip and sever a blood vessel using a single instrument. The instrument can then be used to continue to sever and cauterize small blood vessels, membranes, adhesion bands, etc. by application of heat up to the next large blood vessel where the appropriate ligating clips may be applied to the blood vessel, the blood vessel is then severed as before, and the operation continued.

DETAILED DESCRIPTION OF THE INVENTION

In order to more fully understand the invention, reference should be made to the following detailed description taken in connection with the accompanying drawings wherein like numerals depict like parts, and wherein.

Figure 1:
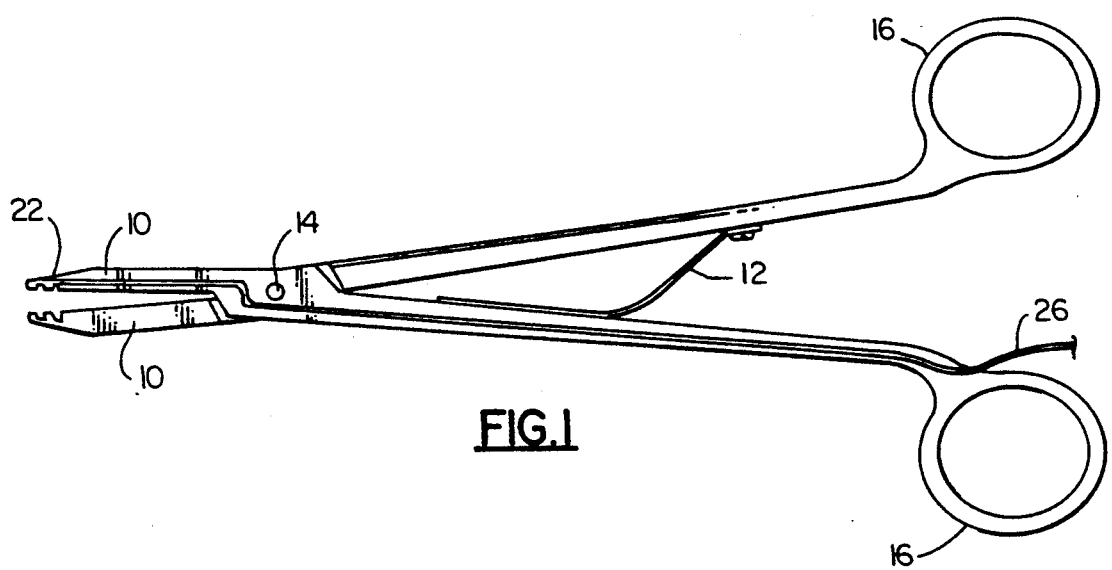
FIG. 1 shows a side elevational view of a clip applicator and cutting and cauterizing surgical instrument, showing the clip applicator jaws in open position, made in accordance with the present invention.
Figure 2:
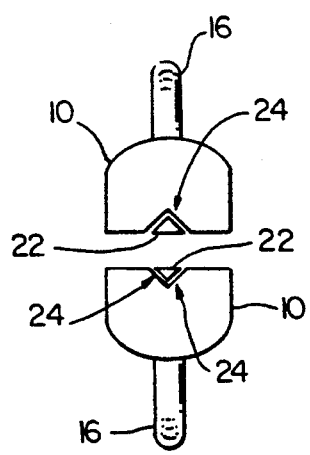
FIG. 2 is an end view in cross section of the surgical instrument, shown in FIG. 1, and showing details of the clip applicator jaws.

Referring now to FIGS. 1 and 2, the combination clip applicator and cutting and cauterizing surgical instrument has a pair of clip closing jaws 10 of the type shown in U.S. Pat. No. 3,439,523. Jaws 10 are urged to a normally open or spaced-apart position by means of a spring member 12, and are pivotally moveable around a pivot pin 14 into a closed position by cooperating handles 16. Jaws 10 close on the plane of FIG. 1. A heating source 22 such as a laser radiation transmission means, e.g. an optical fiber, is operatively disposed within a groove 24 in one or both jaws 10 and is connected via a power supply lead 26 to laser energy source (not shown) of conventional construction. Preferably heating source 22 comprises a bundle of optical fibers in which the fiber ends are spread so as to produce a line of laser light energy between the jaws. The heat source 22 shown is capable of producing and directing sufficient heat energy to sever and cauterize vessels, membranes, etc. During the clip operating portion of the use of the surgical instrument heat source 22 may be deactivated.

In use, ligating clips are applied in spaced relation to a blood vessel. The heat source 22 is then activated and directed between the applied clips onto the blood vessel to be severed. The same instrument may be used to sever and cauterize simultaneously smaller blood vessels without application of clips. Thus, the device of FIGS. 1 and 2 may provide the sole surgical instrument means necessary to ligate, sever and cauterize blood vessels.

Figure 3:
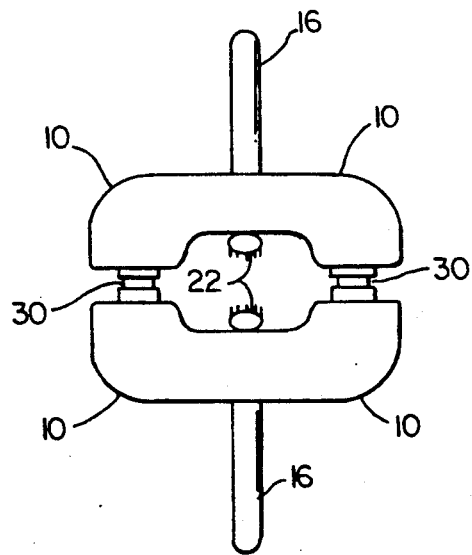
FIG. 3 is a view similar to FIG. 2, of an alternative form of clip applicator and cutting and cauterizing surgical instrument made in accordance with the present invention.

In another form of the invention, shown in FIG. 3, the clip applicator jaws comprise a spaced pairs of jaws 10 for simultaneously applying a pair of ligating clips 30. In this embodiment the heating source 22 is operatively disposed between and adjacent the pairs of jaws 10, and may comprise either a laser radiation transmission means as before, or heat source 22 may comprise a hot wire means. The form of invention shown in FIG. 3 is that a vessel may be ligated and severed in a single step without the need to reposition the instrument.

Figure 4:
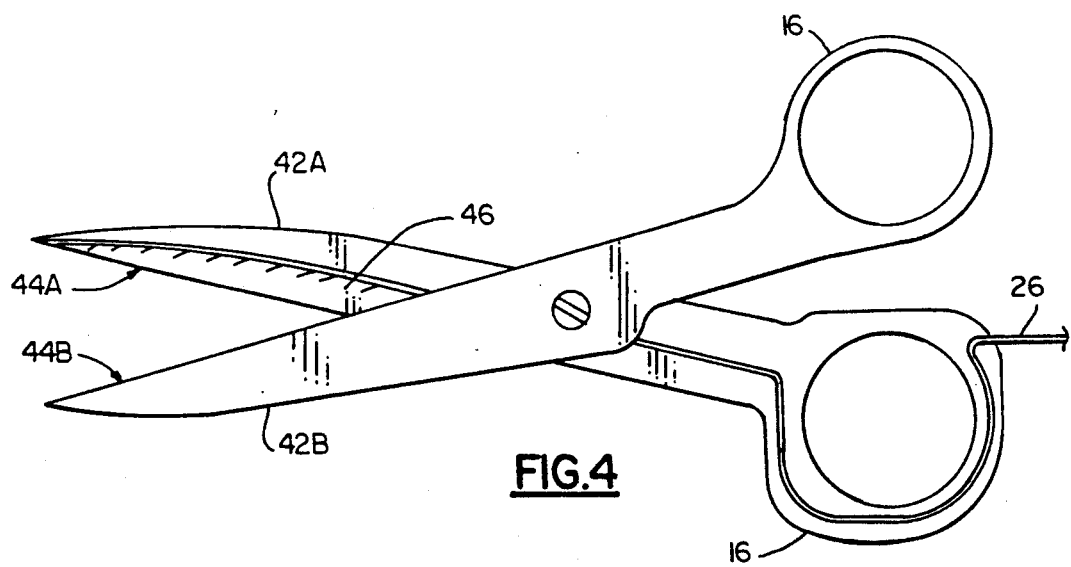
FIGS. 4 and 5 are side views of still other forms of surgical instrument comprising a cutting and/or cauterizing scissors made in accordance with the present invention.

Referring now to FIG. 4 in which another form of the invention is shown, the instrument is in the form of a scissors comprising a pair of opposed pivotally joined blades 42A,42B, each having opposed cutting edges 44A,44B, respectively, for cutting the tissue. As before, a heat source such as a laser radiation transmission means is carried operatively disposed on one or both the blades for cauterizing. The blade or blades incorporating the laser radiation transmission means preferably will be formed from a material such as quartz or sapphire which is transparent to the radiation emitted by the laser, for example, as taught by U.S. Pat. No. 4,126,136, to Auth et al. Preferably the laser radiation transmission means 46 will be elongated and approximately the same length as the cutting edge or edges of the scissors.

Figure 5:
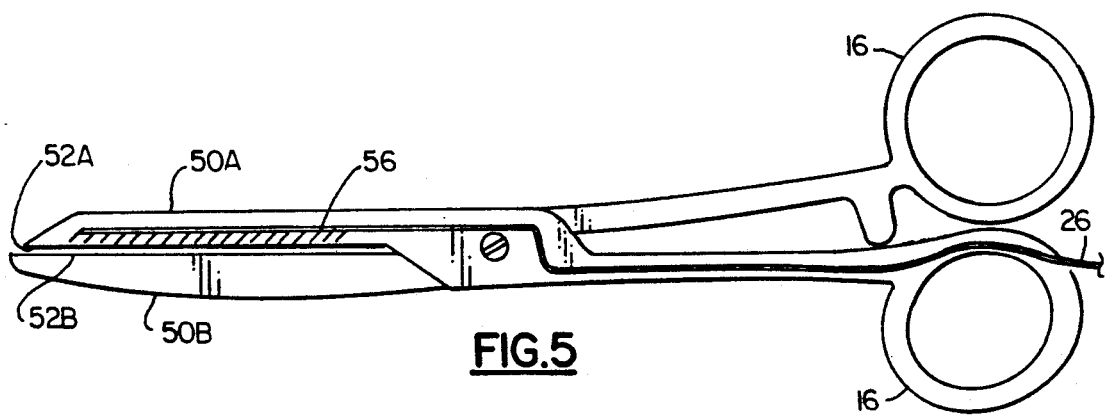

In another form of the invention shown in FIG. 5, the instrument comprises scissors-like opposed pivotally hinged jaws 50A,50B in which one of the jaws has a sharp blade edge 52A, and the other jaw has a blunt anvil edge 52B. As before, a heat source such as a laser radiation transmission means 56 is carried operatively disposed on one or both jaws 50A,50B. A feature and advantage of the embodiment shown in FIG. 5 is that the instrument may be employed for cutting and cauterizing as before, and the tip of blunt jaw 50B also may be employed for peeling or lifting tissues.

Figure 6:
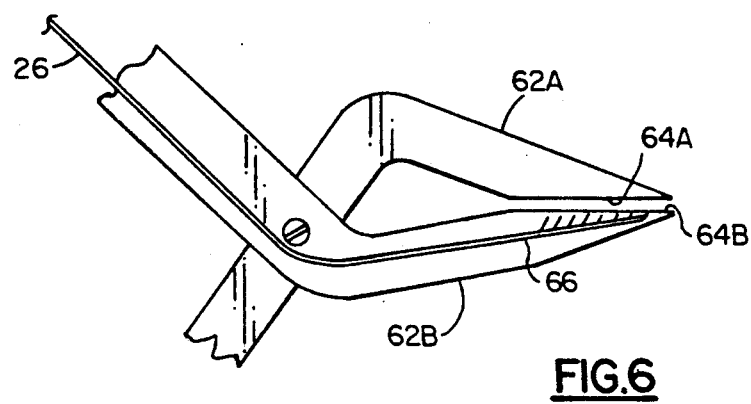
FIG. 6 is a side view of still another form of surgical instrument comprising peeling and cauterizing forceps made in accordance with the present invention.

In yet another embodiment of the invention shown in FIG. 6, the instrument comprises a forceps or tweezers-type configuration comprising a pair of opposed pivotally hinged elongated jaw members 62A,62B, both having blunt edges 64A,64B. As before a heat source such as a laser radiation transmission means 66 is carried operatively disposed on one or both jaw members 62A,62B. One skilled in the art will recognize that the embodiment of the invention shown in FIG. 5 is particularly useful for peeling and cauterizing membranes.

Various changes may be made in the above invention without departing from the spirit and scope thereof. For example, the instrument may be cooled by providing coolant channels (not shown) in the interior of the blades and circulating coolant, e.g. water or refrigerant, through the channels in order to prevent possible heat buildup in the instrument. Also, if desired, an irrigating fluid can be used to control temperature and also to assist in irrigating the surgery all in known manner.

A particular feature and advantage of the present invention which results from the combination of a ligating clip applicator and a heat source is that it permits a surgeon to rapidly perform multiple clip and cut operations without the usual inefficiencies of having to remove and reposition instruments. Another feature and advantage of the present invention, and one which results from the incorporation of a heat source in a surgical scissors is that the control and straight cut advantages of surgical scissors and rapid cut and cauterizing advantages of laser or hot wire scalpels are achieved in a single surgical instrument.

The surgical instrument in accordance with the present invention may be made in a variety of shapes and sizes and may advantageously be used in open surgery, or the instrument may be constructed in miniaturized form so that it may be passed through a laparoscope and advantageously employed in laparoscopic procedures. Still other changes will be obvious to one skilled in the art.

I claim:

1. A surgical instrument comprising a pair of opposed jaw members, at least one of which jaw member is moveable with respect to the other jaw member, and including a heat source operatively disposed on or adjacent at least one of said jaw members for cutting and/or cauterizing during the performance of surgery, wherein said jaw members are dimensioned to receive and hold ligating clips, and wherein said jaw members are moveable between a clip applying open position, and a clip closing position.

2. A surgical instrument according to claim 1, wherein the clip applying jaw members are moveable in a plane, and said heat source is disposed to direct heat energy in said plane.

3. A surgical instrument according to claim 1, wherein at least one of said jaws has a sharpened cutting edge.

4. A surgical instrument according to claim 3, wherein said heat source comprises an optical fiber waveguide for delivering laser radiation from a laser energy source.

5. A surgical instrument according to claim 4, wherein at least one of said jaw members is formed of a material transparent to radiation emitted by said laser energy source.

6. A surgical instrument according to claim 5, wherein said transparent material is selected from the group consisting of quartz and sapphire.

7. A surgical instrument according to claim 7, wherein said jaws have opposed blunt edges.

8. A surgical instrument according to claim 1, wherein said cutting and/or cauterizing heat source comprises a hot wire element.

* * * * *

UNITED STATES PATENT AND TRADEMARK OFFICE
CERTIFICATE OF CORRECTION

PATENT NO. : 5,147,356
DATED : SEPTEMBER 15, 1992
INVENTOR(S) : Nayantara BHATTA It is certified that error appears in the above-identified patent and that said Letters Patent is hereby corrected as shown below:

Claim 1, Col. 4, line 29, "member" should be --members--.

Claim 2, Col. 4, line 39, "the" should be deleted and --said-- inserted therein.

Claim 7, Col. 4, line 56, "7" should be --1--.

Signed and Sealed this

Twenty-eighth Day of September, 1993

Attest:

BRUCE LEHMAN

*Attesting Officer*　　　　*Commissioner of Patents and Trademarks*